US012788769B2

(12) United States Patent
Varenna

(10) Patent No.: US 12,788,769 B2
(45) Date of Patent: Nov. 10, 2026

(54) USE OF NERIDRONIC ACID OR OF ITS SALT FOR THE TREATMENT OF OSTEOARTHROSIS

(71) Applicant: ABIOGEN PHARMA S.P.A., Loc. Ospedaletto (IT)

(72) Inventor: Massimo Varenna, Ospedaletto (IT)

(73) Assignee: ABIOGEN PHARMA SPA, Loc. Ospedaletto (IT)

( * ) Notice: Subject to any disclaimer, the term of this patent is extended or adjusted under 35 U.S.C. 154(b) by 697 days.

(21) Appl. No.: 18/192,094

(22) Filed: Mar. 29, 2023

(65) Prior Publication Data

US 2023/0233585 A1 Jul. 27, 2023

Related U.S. Application Data

(63) Continuation of application No. 15/514,651, filed as application No. PCT/IB2015/057929 on Oct. 15, 2015, now abandoned.

(30) Foreign Application Priority Data

Oct. 15, 2014 (IT) .......................... MI2014A001794

(51) Int. Cl.
*A61K 31/663* (2006.01)
*A61K 9/00* (2006.01)

(52) U.S. Cl.
CPC .......... *A61K 31/663* (2013.01); *A61K 9/0019* (2013.01)

(58) Field of Classification Search
CPC ............................ A61K 31/663; A61P 9/0019
See application file for complete search history.

(56) References Cited

U.S. PATENT DOCUMENTS 9,867,839 B2 1/2018 Tabuteau
2001/0006960 A1 7/2001 Mesnil et al.
2004/0063670 A1 4/2004 Fox et al.

FOREIGN PATENT DOCUMENTS

WO 2005074944 A1 8/2005
WO 2005107751 A1 11/2005
WO 2007092338 A2 8/2007
WO 2011097269 A1 8/2011
WO 2015184003 A1 12/2015

OTHER PUBLICATIONS

"Entitlement Eligibility Guidelines: Osteoarthrosis/Osteoarthritis," Veterans Affairs, Canada, Feb. 2005, pp. 1-26.
Adami S., et al., "Short-term intravenous therapy with neridronate in Paget's disease", Clinical and Experimental Rheumatology, Pacini, Pisa IT, vol. 20, No. 1, Jan. 1, 2002, pp. 55-58.
Benucci M., et al., "Effects of monthly intramuscular neridronate in rheumatic patients in chronic treatment with low-dose glucocorticoids", Clinical and Experimental Rheumatology 2009; 27:567-573.
Bollet, A.J., "Edema of the bone marrow can cause pain in osteoarthritis and other diseases of bone joints", Ann. Intern. Med. 2001; 134:591-593.
Carvalho De Castro A.P., et al., "Zoledronic acid to treat complex regional pain syndrome type I in adult. Case report", Rev. Dor. Sao Paulo, Jan.-Mar. 2011, 12(1):71-73.
Corrado, et al., "Neridronate and human osteoblasts in normal osteoporotic and ostearthritic subjects", Clinical Rheumatology; Journal of the International League of Associations for Rheumatology, Spingren-Verlag, LO, vol. 24, No. 5, Oct. 1, 2005, pp. 527-534.
Del Grande F. et al., "Bone marrow lesions: a systematic diagnostic approach", Indian Journal of Radiology and Imaging, Aug. 2014, vol. 21, issue 3, pp. 279-287.
Dowd G.S.E., et al., "Complex regional pain syndrome with special emphasis on the knee," J Bone Joint Surg (Br) 2007; 89-B:285-90.
Gatti D., et al., "Neridronic acid for the treatment of bone metabolic diseases," Expert Opin Drug Metab Toxicol (2009) 5(10):1305-1311.
Gatti D., et al., "New bisphosphonates in the treatment of bone diseases", Drug & Aging, 1999, Oct. 15(4):285-296.
Laslett L.L., et al., "Zoledronic acid reduces knee pain and bone marrow lesions over 1 year: a randomised controlled trial," Ann Rheum Dis 2012:71:1322-1328.
Laslett, L.L., et al., "Zoledronic acid reduces knee pain and bone marrow lesions over 1 year: a randomised controlled clinical trial", Ann Rheum Dis 2012; 71:1322-1328.
Laslett, LL et al., "Effect of bisphosphonate use in patients with symptomatic and radiographic knee osteoarthritis: data from the Osteoarthritis initiative", Annals of the Rheumatic Diseases, 73(5), pp. 824-830 (2014).
Muratore M., et al.l, "Il neridronato nel trattamento dell'algodistrofia simpatica riflessa dell'anca: confronto in aperto con il clodronato", Progressi in reumatologia v. 5, suppl. 1, (2004): 89.
Office Action issued on Dec. 5, 2017 from Singapore Patent Office in a counterpart application.
Petition for Post Grant Review of U.S. Pat. No. 9,867,839 of Oct. 16, 2018.
Rossini M., et al., "Intra-articular clodronate for the treatment of knee osteoarthritis: dose ranging study v. hyaluronic acid," Rheumatology 2009;48:773-778.
Search Report and Written Opinion of PCT/IB2015/057929 of Jan. 27, 2016.
Siebelt M., et al., "Inhibited osteoclastic bone resorption through alendronate treatment in rats reduces severe osteoarthritis progression", Bone, vol. 66, Jun. 2014, pp. 163-170.
Singapore Office Action issued for correspondent patent application 11201702574X on Jan. 22, 2019.
Spector T., et al., "Effect of risedronate on joint structure and symptoms of knee osteoarthritis: results of the BRISK randomized, controlled trial", Arthritis Research, Current Science, London, GB, vol. 7, No. 3, Mar. 24, 2005, pp. R625-R633.

(Continued)

*Primary Examiner* — Alicia L Otton
(74) *Attorney, Agent, or Firm* — Silvia Salvadori, P.C.; Silvia Salvadori

(57) ABSTRACT

The use of neridronic acid or a salt thereof in the treatment of osteoarthritis is described. In particular, neridronic acid or a salt thereof has been shown to be able to reduce significantly the symptoms of osteoarthritis, such as pain and physical and mobility disabilities, as well as subchondral bone marrow lesions underlying the onset of such symptoms.

6 Claims, 2 Drawing Sheets

(56) References Cited

OTHER PUBLICATIONS

Varenna M. "Efficacy study of neridronate to treat painful osteoarthritis of the knee with bone marrow lesions," https://clinicaltrials.gov/ct2/show/NCT01803360, Mar. 4, 2013.
Varenna M., et al., "Treatment of complex regional pain syndrome type I with neridronate: a randomized, double-blind, placebo-controlled study," Rheumatology 2013;52:534-542.
Varenna, M., "Treatment of complex regional pain syndrome type I with neridronate: a randomized, double-blind, placebo-controlled study.", Rheumatology, Mar. 2013, vol. 52, No. 3, pp. 534-542.
Zaspel J. et al., "Treating CRPS I in the early stage-cortisone (methyl prednisolone) versus bisphosphonate (zoledronic acid)", German Congress for Orthpedics and Trauma Surgery, 71st annual conference of the German Association for Trauma Surgery, 93rd annual conference of the German Association for Orthopedics and Trauma Surgery, and the 48th annual conference of the Professional Association of Specialists in Orthopedics and Trauma Surrgy, Oct. 27, 2007.

USE OF NERIDRONIC ACID OR OF ITS SALT FOR THE TREATMENT OF OSTEOARTHROSIS

This application is a Continuation of U.S. Ser. No. 15/514,651 filed on Mar. 27, 2017, which is a U.S. national stage of PCT/IB2015/057929 filed on 15 Oct. 2015, which claims priority to and the benefit of Italian Application No. MI2014A001794 filed on 15 Oct. 2014, the contents of which are incorporated herein by reference in their entireties.

FIELD OF THE INVENTION

The present invention relates to the use of neridronic acid or a salt thereof in the treatment of osteoarthritis. In particular, neridronic acid or a salt thereof has been shown to be able to reduce significantly the symptoms of osteoarthritis, such as pain and physical disabilities, as well as subchondral bone marrow lesions underlying the onset of such symptoms.

BACKGROUND ART

Osteoarthritis (OA) is, along with hypertension, the disease with the highest prevalence in the world over fifty years old population and is the most common cause of chronic disability. Given the epidemiological importance of said disease, to date there are no recognized effective therapeutic strategies capable of modifying the disease course, slowing/stopping the anatomical progression of joint damage.

The therapeutic objectives which can be currently pursued are therefore only aimed at reducing painful symptoms and functional deficits associated therewith.

Despite the several guidelines and consensus documents published so far (Nelson A E et al. Sem Arthritis Rheum, 2014), the optimal strategies in the clinical management of pain symptoms in patients suffering from arthritis are not yet unanimous. This is due to different confusing aspects: firstly, due to the typical features of arthritic pain, usually floating over time with possible intense painful recrudescence lasting weeks/months capable of permanently affecting the degree of disability of the patient; secondly, due to the large number of proposed therapeutic approaches, whether based on physical (non-pharmacological), pharmacological (intra-articular and systemic) or surgical therapies.

At present, the non-pharmacological approach, understood as joint saving strategy (functional limitation and reduction of body weight on bearing joints) and which may involve the use of specific tools (braces, splints, Canadian sticks) and the kinesitherapic approach (maintaining the muscle tone/trophism and joint mobility through specific rehabilitative exercises) turns out to be the most unanimous therapeutic strategy, despite the clear limitations of a modest impact on pain symptoms. Similarly, other instrumental physical therapies such as the local application of radiation or ultrasonographic waves does not have an unanimous utility and above all, is poorly effective at the level of joint sites frequently affected by arthritis, such as the large joints of the lower limb (hip and knee).

The surgical approach is solely aimed at a preventive (correction of anatomic defects which cause an altered load) or radical strategy, such as prosthetic joint replacement, where possible, of joints severely anatomically damaged.

The pharmacological strategy is the strategy usually and widely used in the management of arthritis pain. In these terms, the need for a chronic or in any case prolonged therapy, the old age of the patient and thus the frequent presence of other diseases and relevant treatments represent the obstacles which the clinician must systematically deal with. The most conservative approach refers to the use of minor analgesics such as paracetamol, which usually shows a fair risk-benefit profile when used at the dosages usually prescribed for treating chronic pain symptoms, i.e. minor pain experienced daily by the patient, while it is only modestly effective in treating middle/high intensity arthritic pain. Conversely, major analgesics (opioids), i.e. with a stronger analgesic effect, are difficult to use due to the high rate of adverse events observed in elderly patients.

The use of nonsteroidal anti-inflammatory drugs (NSAIDs) is affected by the tolerance limits related to the need for continued use in elderly patients, i.e. the risk of gastrointestinal side effects for traditional NSAIDs and of cardiovascular adverse events as regards next generation NSAIDs (e.g. Coxib).

Similarly, to date the intra-articular administration of drugs does not have a widely unanimous consensus, both with regard to the use of cortisone derivatives, due to their chondrolesive potential when administered at high dosages or high frequency, and with regard to the use of hyaluronate, which does not seem to be able to provide a substantial benefit in the treatment of painful symptoms, particularly in the treatment of acute painful poussées.

Finally, a possible therapeutic role of bisphosphonates (briefly "BPs") was also investigated.

A number of studies have been published on the subject, which actually cover only retrospective assessments of possible effects on osteoarthritis, exclusively based on data recorded for certain BPs administered in the treatment of postmenopausal osteoporosis.

BPs are a class of drugs widely and specifically used in the treatment of postmenopausal osteoporosis and other skeletal disorders characterized by an altered bone metabolism.

Among the various prospective studies carried out in order to evaluate said possible therapeutic role of some BPs on the anatomical progression of osteoarthritis, in particular the studies on aminobisphosphonate risedronate conducted by Bingham CO (Arthritis Rheum 54, 2006, 3494-3507) and Spector T D et al. (Arthritis Research Ther 2005, 7: R625-33) are significant, but they did not provide positive results in this regard. In fact, according to the authors of said studies, it was not possible to find any difference, in terms of efficacy of treatment in pain symptoms, between the group of patients treated with the BPs and the group of patients treated with placebo, at any of the dosages tested (5, 15, 35 and 50 mg).

In particular, Spector T D et al. point out that the preliminary clinical data obtained on the effect of risedronate one year after treatment were not then replicated and confirmed in the subsequent study extended to two years of treatment.

Therefore, even the possibility of a therapeutic use of BPs, and in particular of aminobisphosphonates, in the treatment of OA, and particularly of pain symptoms and physical disabilities of patients suffering from OA, does not appear to be a viable strategy. Therefore, it is an object of the present invention to find an effective remedy capable of acting on the conditions of an arthritic patient in order to improve the symptoms thereof, such as pain and disability.

SUMMARY OF THE INVENTION

Said object has been achieved by using neridronic acid or a salt thereof in the treatment of osteoarthritis as stated in claim 1.

In particular, neridronic acid or a salt thereof has been shown to be able to reduce significantly the symptoms of osteoarthritis, such as pain and disabilities, as well as subchondral bone marrow lesions underlying the onset of such symptoms.

In another aspect, the present invention relates to a pharmaceutical composition to be administered intravenously, comprising said neridronic acid or a salt thereof for use in the treatment of osteoarthritis, and to pharmaceutically acceptable vehicles for intravenous administration.

In a further aspect, the present invention relates to a vial or bottle for intravenous administration comprising neridronic acid or a salt thereof for use in the treatment of osteoarthritis.

In an even further aspect, the present invention relates to a pharmaceutical composition to be administered intramuscularly, comprising said neridronic acid or a salt thereof for use in the treatment of osteoarthritis, and to pharmaceutically acceptable vehicles for intramuscular administration.

In another aspect, the present invention relates to a vial or bottle for intramuscular administration comprising neridronic acid or a salt thereof for use in the treatment of osteoarthritis.

BRIEF DESCRIPTION OF THE DRAWINGS

The characteristics and the advantages of the present invention will become apparent from the following detailed description, from the working examples provided for illustrative purposes, and from the annexed Figures wherein.

DETAILED DESCRIPTION OF THE INVENTION

Figure 1:
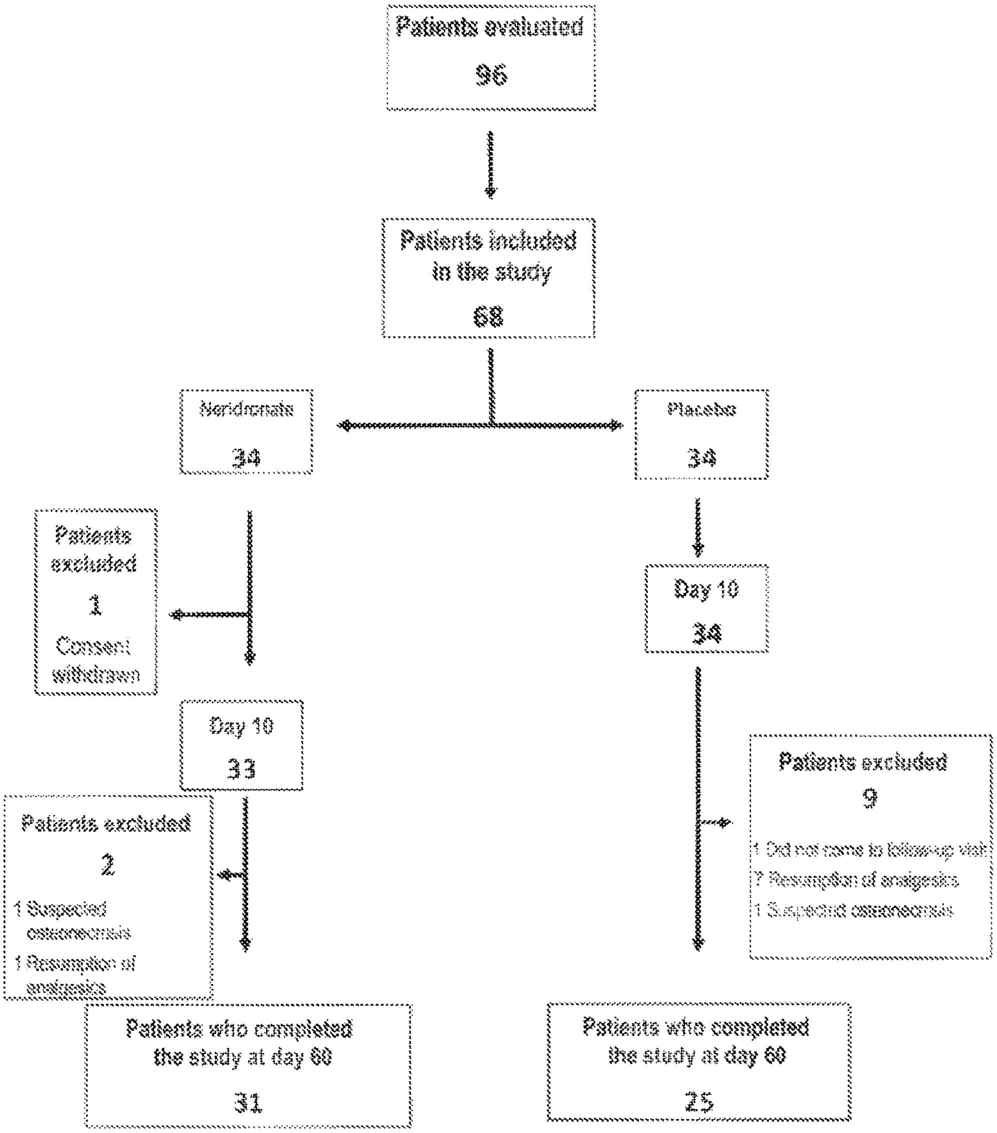
FIG. 1 shows the apportionment of patients recruited for the study of Example 1.

The invention thus relates to neridronic acid or a salt thereof for use in the treatment of osteoarthritis (briefly, "OA").

In particular, as it will be also apparent from the examples given hereinafter, neridronic acid or a salt thereof has been shown to be able to reduce significantly the symptoms of osteoarthritis, such as pain and physical disabilities, as well as the size of subchondral bone marrow lesions.

Therefore, it was surprisingly found that neridronic acid or a salt thereof has proved to be able to successfully treat osteoarthritis by relieving mild, moderate or severe symptoms ascribable thereto, in particular moderate or severe symptoms.

Neridronic acid or a salt thereof has been shown to be able to successfully treat mild, moderate or severe pain symptoms in patients suffering from osteoarthritis, particularly OA of the hip, knee or hand, especially OA of the knee.

Moreover, it was surprisingly found that neridronic acid or a salt thereof has shown to be able to successfully treat osteoarthritis by relieving joint stiffness and improving mobility and physical functionality.

In particular, neridronic acid or a salt thereof has been shown to be able to successfully treat joint stiffness, by improving mobility and physical functionality in patients suffering from OA of the hip, knee or hand, especially OA of the knee.

As it will be clear from the examples given hereinafter, neridronic acid or a salt thereof has been shown to reduce significantly pain intensity in patients with OA, as well as joint stiffness, and advantageously improve mobility and physical functionality even after more than 50 days since the end of treatment.

Neridronic acid or a salt thereof has further proved to be able to treat pain in patients with OA during acute painful poussée.

In fact, it was surprisingly found that neridronic acid or a salt thereof has proved to be able to reduce the sizes and extents of bone marrow lesions associated with arthritis pain symptoms.

The examples given hereinafter show that neridronic acid or a salt thereof can successfully improve the pattern of subchondral bone marrow lesions detectable by nuclear magnetic resonance (NMR).

For the purposes of the present invention, the term "neridronic acid or a salt thereof" is understood to include all polymorphic forms, both amorphous and crystalline, as well as co-crystalline and anhydrous, hydrated and solvate forms.

Preferably, said neridronic acid is in the form of a salt. Said neridronic acid salt is alkaline or alkaline-earthy neridronate salt, such as sodium neridronate or potassium neridronate, quaternary ammonium salt of neridronate or a mixture thereof.

In a preferred embodiment, said neridronic acid salt is sodium neridronate.

Neridronic acid or a salt thereof is to be preferably administered at a dosage of 10-500 mg.

Said neridronic acid or a salt thereof can be administered orally, intramuscularly, intravenously, intraarticularly, transdermally, subcutaneously or topically.

Preferably, said neridronic acid or a salt thereof is to be administered intravenously.

Neridronic acid or a salt thereof is to be administered intravenously, preferably at a dosage of 25-400 mg. More preferably, said neridronic acid or a salt thereof is to be administered at least 2 times, with at least 1 day between an administration and a subsequent one.

For the purposes of the present invention, the term "day" means a period of 24±2 hours. Therefore, said neridronic acid or a salt thereof can be used according to dosing regimens comprising daily administrations, alternate-day administrations, or administrations every at least two or three days and beyond.

Preferably, said neridronic acid or a salt thereof is to be administered intravenously at a dosage of 50-200 mg, at least 2 times over a period of 5-15 days, with at least 1 day between an administration and a subsequent one.

In preferred embodiments, said neridronic acid or a salt thereof is to be administered intravenously at a dosage of 50-200 mg, at least 3 times over a period of 5-15 days, with at least 2 days between an administration and a subsequent one.

In other preferred embodiments, said neridronic acid or a salt thereof is to be administered intravenously at a dosage of 70-150 mg, 4 times over a period of 8-12 days, with 2 days between an administration and a subsequent one.

Alternatively, said neridronic acid or a salt thereof is to be administered intravenously at a dosage of 70-150 mg, 4 times over a period of 8-12 days, with 3 days between an administration and a subsequent one.

In the most preferred embodiments, said neridronic acid or a salt thereof is to be administered intravenously at a dosage of 90-110 mg, 4 times over a period of 10 days, with 3 days between an administration and a subsequent one.

In an even more preferred embodiment, said neridronic acid is in the form of sodium salt (sodium neridronate) to be administered intravenously at a dosage of 90-110 mg, 4 times over a period of 10 days, with 3 days between an administration and a subsequent one.

In a further even more preferred embodiment, said neridronic acid in the form of sodium salt (sodium neridronate) is to be administered intravenously at a dosage of 100 mg of neridronic acid, 4 times over a period of 10 days, with 3 days between an administration and a subsequent one. In this way, the intravenous administration can be carried out on days 1, 4, 7 and 10 of treatment.

As can be seen from the example below, the results of the randomized controlled study demonstrated that sodium neridronate can be used effectively for treating patients with OA. In particular, the results of this study demonstrated that sodium neridronate can be used effectively to reduce the mild, moderate or severe pain symptoms, and even more specifically moderate or severe symptoms, in patients with OA.

Specifically, sodium neridronate can be used effectively to reduce pain symptoms in patients with OA having basal VAS≥(greater than or equal to) 30 mm.

Specifically, a course of sodium neridronate administered intravenously can be used effectively to treat patients with OA, and in particular to reduce mild, moderate or severe pain symptoms in patients with OA.

In particular, the study demonstrated that a course of sodium neridronate administered intravenously reduces the pain intensity in patients with symptomatic OA of the knee.

The study also demonstrated that the size and extent of BMLs decreased significantly in patients treated with sodium neridronate compared to patients treated with placebo only. That is, sodium neridronate can be used effectively for treating patients with OA undergoing acute painful poussées, thus reducing the extent of bone marrow lesions.

In addition, the study demonstrated that the treatment of patients with OA with sodium neridronate allowed an effective and long lasting symptomatic treatment, and thereby pain control, even after more than 50 days since the end of treatment.

The advantageous results achieved with the present invention in the treatment of osteoarthritis, especially in the treatment of mild, moderate or severe pain symptoms in patients with OA are therefore evident, especially considering that these results were unexpected in view of the prior art related to BPs, particularly to aminobisphosphonates, such as risedronate.

In preferred embodiments, said neridronic acid or a salt thereof is in the form of an aqueous solution of neridronic acid or a salt thereof. Said aqueous solution is preferably isotonic or hypotonic, even more preferably hypotonic.

Said neridronic acid or a salt thereof is further preferably present as a unit dose comprising 1-10 ml of aqueous solution in a vial or bottle, preferably a glass vial or bottle. Preferably, said unit dose comprises 2, 5 or 8 ml of an aqueous solution in a vial or bottle. Preferably, said unit dose comprises 70-150 mg of neridronic acid or a salt thereof.

In a particularly preferred embodiment, said unit dose comprises 100 mg of neridronic acid or comprises a salt thereof in an amount equivalent to 100 mg of neridronic acid. Therefore, according to a further aspect thereof, the present invention also relates to a vial or bottle for intravenous administration comprising neridronic acid or a salt thereof for use in the treatment of osteoarthritis.

Preferably, said vial or bottle comprises a unit dose of 70-150 mg of neridronic acid or a salt thereof.

More preferably, said vial or bottle comprises 100 mg of neridronic acid or comprises a salt thereof in an amount equivalent to 100 mg of neridronic acid.

Advantageously, said vial or bottle is in a ready-to-use form.

In another aspect, the present invention relates to a pharmaceutical composition comprising said neridronic acid or a salt thereof for use in the treatment of osteoarthritis, and pharmaceutically acceptable vehicles for the oral, intramuscular, intravenous, intra-articular, transdermal, sub-cutaneous or topical administration.

Specifically, said pharmaceutical composition comprising said neridronic acid or a salt thereof, and pharmaceutically acceptable vehicles for the oral, intramuscular, intravenous, intra-articular, transdermal, sub-cutaneous or topical administration, is for use in the treatment of osteoarthritis of the hip, knee or hand, preferably it is for use in the treatment of ostcoarthritis of the knee.

Preferably, said pharmaceutical composition is to be administered intravenously and comprises said neridronic acid or a salt thereof for use in the treatment of osteoarthritis, and pharmaceutically acceptable vehicles for intravenous administration.

Pharmaceutically acceptable vehicles suitable for intravenous administration are for example, pH adjusters, isotonicity adjusters, stabilizers, chelating agents, preservatives and antioxidants.

Preferred pH adjusters are citric acid, sodium citrate, sodium acetate, boric acid, sodium borate, sodium bicarbonate, phosphoric acid and salts thereof, even more preferably citric acid and sodium citrate (citrate buffer) and sodium bicarbonate.

Among isotonicity adjusters, sodium chloride is preferred.

Among stabilizers, mannitol, dextran or mixtures thereof are preferred.

Among chelating agents, EDTA or a salt thereof, such as sodium EDTA, is preferred.

Among antioxidants, sodium metabisulphite, potassium metabisulphite, sodium bisulphite, butylated hydroxy anisole (BHA), butylated hydroxy toluene (BHT), ascorbic acid and sodium ascorbate are preferred.

Among preservatives, benzyl alcohol, methyl paraben and propyl paraben are preferred. In a preferred embodiment, said pharmaceutical composition to be administered intravenously comprises sodium neridronate for use in the treatment of osteoarthritis, citrate buffer and sodium chloride.

In another preferred embodiment, said pharmaceutical composition to be administered intravenously comprises sodium neridronate for use in the treatment of osteoarthritis, sodium bicarbonate and sodium chloride.

In other preferred embodiments, in said pharmaceutical composition to be administered intravenously, said neridronic acid or a salt thereof is the only active ingredient present for use in the treatment of osteoarthritis.

Alternatively, said pharmaceutical composition to be administered intravenously consists of said neridronic acid or a salt thereof for use in the treatment of osteoarthritis, and pharmaceutically acceptable vehicles for intravenous administration.

Preferably, the pharmaceutical composition is in the form of an aqueous solution. Said aqueous solution is preferably isotonic or hypotonic, even more preferably hypotonic.

Said pharmaceutical composition is further preferably present as a unit dose comprising 1-10 ml of aqueous solution in a vial or bottle, preferably a glass vial or bottle. Preferably, said unit dose comprises 2.5 or 8 ml of an aqueous solution in a vial or bottle. Preferably, said unit dose comprises 70-150 mg of neridronic acid or a salt thereof.

In a particularly preferred embodiment, said unit dose comprises 100 mg of neridronic acid or comprises a salt thereof in an amount equivalent to 100 mg of neridronic acid. According to a further aspect, the present invention therefore also relates to a vial or bottle for intravenous administration comprising neridronic acid or a salt thereof for use in the treatment of osteoarthritis.

Preferably, said vial or bottle comprises a unit dose of 70-150 mg of neridronic acid or a salt thereof.

More preferably, said vial or bottle comprises 100 mg of neridronic acid or comprises a salt thereof in an amount equivalent to 100 mg of neridronic acid.

Advantageously, said vial or bottle is in a ready-to-use form.

Preferably, said neridronic acid or a salt thereof is sodium neridronate for use in the treatment of osteoarthritis.

More preferably, said vial or bottle is for the intravenous administration of sodium neridronate for use in the treatment of osteoarthritis.

Alternatively, said neridronic acid or a salt thereof is to be administered intramuscularly. Neridronic acid or a salt thereof is to be administered intramuscularly preferably at a dosage of 10-100 mg.

Preferably, said neridronic acid or a salt thereof is to be administered intramuscularly at a dosage of 15-50 mg, more preferably at a dosage of 25 mg of neridronic acid or at an equivalent dosage of a salt thereof, preferably sodium neridronate.

In the particularly preferred embodiments, said neridronic acid or a salt thereof is sodium neridronate to be administered intramuscularly at a dosage of 15-50 mg, 1 to 20 times over a period of 1-30 days.

In the most preferred embodiments, said neridronic acid or a salt thereof is sodium neridronate to be administered intramuscularly at a dosage of 25 mg of neridronic acid, 1 to 16 times over a period of 1-16 days.

In an even further aspect, the present invention relates to a pharmaceutical composition to be administered intramuscularly and comprises said neridronic acid or a salt thereof for use in the treatment of osteoarthritis, and pharmaceutically acceptable vehicles for intramuscular administration.

Pharmaceutically acceptable vehicles suitable for intramuscular administration are for example, pH adjusters, isotonicity adjusters, stabilizers, chelating agents, preservatives and antioxidants.

Preferred pH adjusters are citric acid, sodium citrate, sodium acetate, boric acid, sodium borate, sodium bicarbonate, phosphoric acid and salts thereof, even more preferably citric acid and sodium citrate (citrate buffer) and sodium bicarbonate.

Among the isotonicity adjusters, sodium chloride is preferred.

Among the stabilizers, mannitol, dextran or mixtures thereof are preferred.

Among the chelating agents, EDTA or a salt thereof, such as sodium EDTA, is preferred.

Among the antioxidants, sodium metabisulphite, potassium metabisulphite, sodium bisulphite, butylated hydroxy anisole (BHA), butylated hydroxy toluene (BHT), ascorbic acid and sodium ascorbate are preferred.

Among preservatives, benzyl alcohol, methyl paraben and propyl paraben are preferred. In a preferred embodiment, said pharmaceutical composition to be administered intramuscularly comprises sodium neridronate for use in the treatment of osteoarthritis, citrate buffer and sodium chloride.

In another preferred embodiment, said pharmaceutical composition to be administered intramuscularly comprises sodium neridronate for use in the treatment of osteoarthritis, sodium bicarbonate and sodium chloride.

In other preferred embodiments, in said pharmaceutical composition to be administered intramuscularly, said neridronic acid or a salt thereof is the only active ingredient present for use in the treatment of ostcoarthritis.

Alternatively, said pharmaceutical composition to be administered intramuscularly consists of said neridronic acid or a salt thereof for use in the treatment of osteoarthritis, and pharmaceutically acceptable vehicles for intramuscular administration.

Preferably, the pharmaceutical composition is in the form of an aqueous solution of neridronic acid or a salt thereof. Said aqueous solution is preferably isotonic or hypotonic, even more preferably hypotonic.

Said pharmaceutical composition is further preferably present as a unit dose comprising 1-10 ml of aqueous solution in a vial or bottle, preferably a glass vial or bottle. Preferably, said unit dose comprises 2, 5 or 8 ml of an aqueous solution in a vial or bottle. Preferably, said unit dose comprises 10-100 mg of neridronic acid or a salt thereof.

In a particularly preferred embodiment, said unit dose comprises 25 mg of neridronic acid or comprises a salt thereof in an amount equivalent to 25 mg of neridronic acid.

According to a further aspect thereof, the present invention therefore also relates to a vial or bottle for intramuscular administration comprising neridronic acid or a salt thereof for use in the treatment of osteoarthritis.

Advantageously, said vial or bottle is in a ready-to-use form.

Preferably, said neridronic acid or a salt thereof is sodium neridronate for use in the treatment of osteoarthritis.

More preferably, said vial or bottle is for the intramuscular administration of sodium neridronate for use in the treatment of osteoarthritis.

Alternatively, said neridronic acid or a salt thereof is to be administered orally or sublingually.

In yet a further aspect, the present invention relates to a pharmaceutical composition to be administered orally or sublingually and comprises said neridronic acid or a salt thereof for use in the treatment of osteoarthritis, and pharmaceutically acceptable vehicles for oral or sublingual administration.

Suitable pharmaceutically acceptable vehicles for oral or sublingual administration for example are natural starch, partially hydrolyzed starch, lactose, glucose, sucrose, mannitol, sorbitol, cellulose and derivatives thereof, microcrystalline cellulose and derivatives thereof, calcium phosphate, calcium carbonate, calcium sulfate, magnesium stearate, maltodextrin, gelatin, gum tragacanth, arabic gum, xanthan gum, talc, silica, colloidal silica, precipitated silica, magnesium silicates, aluminum silicates, sodium lauryl sulfate, magnesium lauryl sulfate, methacrylate copolymers, and mixtures thereof. Said composition for oral or sublingual administration can be in the form of powder, capsule, tablet, mini-tablet, micro-tablet, granule, microgranule, pellet, multi-particulate or micronized particles. Alternatively, it may be in liquid form, i.e. in solution, dispersion or suspension with suitable pharmaceutically acceptable solvents.

All pharmaceutical compositions described above can be prepared by using methods known in the art according to the route of administration.

A method is also described for the treatment of osteoarthritis, comprising the steps of:

i) providing neridronic acid or a salt thereof, ii) administering a therapeutically effective amount of said neridronic acid or a salt thereof to a patient suffering from osteoarthritis.

In step i), said neridronic acid or a salt thereof can be in the form of an aqueous solution of neridronic acid or a salt thereof, as described above.

Preferably, said neridronic acid or a salt thereof is provided as a unit dose comprising 1-10 ml of aqueous solution in a vial or bottle.

All the above-described advantageous and preferred aspects for use of neridronic acid or a salt thereof are to be understood as similarly advantageous and preferred.

In particular, said method allows the pain symptoms of osteoarthritis to be relieved in a patient suffering from osteoarthritis.

Preferably, in step ii), the administration of a therapeutically effective amount of neridronic acid or a salt thereof to a patient suffering from osteoarthritis relieves mild, moderate or severe symptoms ascribable to osteoarthritis, in particular moderate or severe symptoms.

In particular, said administration relieves mild, moderate or severe pain symptoms in patients suffering from osteoarthritis of the hip, knee or hand, especially OA of the knee. Specifically, said administration effectively reduces pain symptoms in patients with OA having basal VAS≥(greater than or equal to) 30 mm.

Advantageously, said administration relieves joint stiffness and improves the mobility and physical functionality of the patient.

The administration of neridronic acid or a salt thereof reduces pain intensity in patients with OA, as well as joint stiffness and advantageously improves mobility and physical functionality even after more than 50 days since the end of treatment.

More preferably, said administration relieves pain in patients with OA during acute painful poussées.

In addition, the administration of neridronic acid or a salt thereof reduces the size and extent of bone marrow lesions associated with pain symptoms caused by arthritis, particularly in the case of OA of the knee.

A method is also described for the treatment of osteoarthritis, comprising the steps of:

i) providing a pharmaceutical composition comprising neridronic acid or a salt thereof as described above.

ii) administering a therapeutically effective amount of said pharmaceutical composition to a patient suffering from ostcoarthritis.

In step i), said pharmaceutical composition can be in the form of an aqueous solution of neridronic acid or a salt thereof, as described above.

Preferably, said pharmaceutical composition is provided as a unit dose comprising 1-10 ml of aqueous solution of neridronic acid or a salt thereof in a vial or bottle.

All the above-described advantageous and preferred aspects for the pharmaceutical composition of neridronic acid or a salt thereof are to be understood as similarly advantageous and preferred.

In particular, said method allows the pain symptoms of osteoarthritis to be relieved in a patient suffering from osteoarthritis.

Preferably, the administration of a therapeutically effective amount of a pharmaceutical composition of neridronic acid or a salt thereof to a patient suffering from osteoarthritis relieves mild, moderate or severe symptoms ascribable to osteoarthritis, in particular moderate or severe symptoms.

In particular, said administration relieves mild, moderate or severe pain symptoms in patients suffering from osteoarthritis of the hip, knee or hand, especially OA of the knee. Specifically, said administration effectively reduces pain symptoms in patients with OA having basal VAS≥(greater than or equal to) 30 mm.

Advantageously, said administration relieves joint stiffness and improves the mobility and physical functionality of the patient.

The administration of a pharmaceutical composition of neridronic acid or a salt thereof reduces pain intensity in patients with OA, as well as joint stiffness and advantageously improves mobility and physical functionality, even after more than 50 days since the end of treatment.

More preferably, said administration relieves pain in patients with OA during acute painful poussées.

In addition, the administration of a pharmaceutical composition of neridronic acid or a salt thereof reduces the size and extent of bone marrow lesions associated with pain symptoms caused by arthritis, particularly in the case of OA of the knee.

It is understood that all the aspects identified as preferred and advantageous for the use of neridronic acid or a salt thereof are to be deemed similarly preferred and advantageous also for the pharmaceutical compositions, vials, bottles, unit doses and their respective uses, as well as for the methods of treating ostcoarthritis.

All the combinations of preferred aspects of the use of neridronic acid or a salt thereof, the pharmaceutical composition, vial, bottle, unit dose and their respective uses, as well as of the methods of treating osteoarthritis mentioned above are further understood as also described.

Below is a working example of the present invention provided for illustrative purposes.

Example

The aim of this randomized, double-blind, placebo-controlled study was to assess the efficacy of intravenous neridronate in controlling pain in patients with acute painful knee osteoarthritis (OA).

Patients

From March 2013 to January 2014, 96 patients older than 50 years and with a recent onset of knee pain were screened. These patients came from the orthopedic and rheumatologic outpatients services and the emergency department of a tertiary care center devoted to bone and joint diseases. Sixty-eight patients were considered eligible to be recruited when they met the following inclusion criteria: 1) knee OA fulfilling the American College of Rheumatology diagnostic criteria; 2) a radiographic Kellgren-Lawrence grading score ≥2 in the tibiofemoral joint; 3) a continuous knee pain by at least 2 weeks with an onset no longer than three months; 4) a pain intensity greater than 30 mm on a Huskisson's visual analog scale ranging from 0 (no pain) to 100 mm (maximal pain); 5) a knee MR scan showing large (>1 cm according to international criteria) BMLs. Exclusion criteria were related to the presence of inflammatory or metabolic diseases; the presence of routine laboratory abnormalities (comprising calcemia, and glomerular filtration rate, which if altered are capable of increasing the risk of adverse events in patients treated with BPs intravenously); prior treatment with BPs; evidence of significant joint effusion through MRI scan, morphological alterations at the subchondral bone joint profile suggesting osteonecrosis and/or evidence of bursitis or tendonitis; onset of pain related to a specific traumatic event. At the time of recruitment, 58 patients out of 68 (85.3%) were taking or had taken drugs to control pain in the previous three months. The patients were asked not to take any analgesics or nonsteroidal anti-inflammatory drugs (NSAIDs) throughout the study period. All patients gave written consent. The study was approved by the Ethics Committee of the hospital where the study was carried out.

Study Design

After enrolment, patients were randomized to receive placebo or sodium neridronate (Abiogen, Pisa, Italy) 100 mg/8 ml in vials with an identical appearance in a 1:1 ratio. Both sodium neridronate and placebo were diluted in 500 ml of saline isotonic solution and infused in the morning for over 2 hours. The treatment was administered every third day four times starting from day 1 (first infusion) and ending on day 10 (fourth infusion). Throughout the infusion course, serum calcium was assayed before each infusion. The values were adjusted for albumin value of 4.2 g/dL. After 60 days (57-66) from the first infusion, the last clinical assessment was performed. Two months after the end of the study, patients were interviewed by telephone about a possible relapse of pain and the possible resumption of analgesic drugs and/or NSAIDs.

Knee Magnetic Resonance Imaging

High resolution, three-dimensional MRI of the target knee was obtained for each patient before the start of the treatment (1-7 days) and at the end of the study (day 58-69). All MR images were evaluated by a skilled musculoskeletal radiologist who was blinded to the patient's treatment. All MR examinations were performed with a 1.5 T scanner (Magnetom Espree, Siemens) using a dedicated knee coil. Imaging was performed on sagittal, coronal and transverse planes, with a field of view (FOV) of 18 cm and a matrix of acquisition of 256×256. The MR protocol included: spin echo (SE) T1-weighted sequences (repetition time TR 580 ms, echo time TE 12 ms, number of signal averages 2, thickness 3.0 mm, intersection gap 0.5 mm) on sagittal, coronal and transverse planes; SE T2-weighted sequences (TR 4.000 ms, TE 30/100 ms, one signal acquired, thickness 3.0 mm, intersection gap 0.5 mm) on sagittal and transverse planes; PD-weighted sequence with fat/suppression (TR 2800 ms, TE 40 ms, one signal acquired, thickness 3.0 mm, intersection gap 0.5 mm) on coronal plane. Subchondral BMLs were identified as areas of increase signal intensity on fat-suppressed T2-weighted images. Scores were assigned using the Whole-Organ MRI score for knee OA (WORMS) for bone marrow edema. Specifically, BMLs were coded 0-3 in each of 10 subregions of the medial and lateral tibiofemoral compartments and in each of the four subregions of the patellofemoral compartments. For each subregion, the extent of the lesion was assessed following the WORMS scale: 0=absence of edema; 1=less than 25%; 2=25-50%; 3=>50%.

Measures

Primary outcome of the study was the assessment and comparison of changes in pain intensity between the sodium neridronate group and the placebo group along the study. Pain in the affected knee was measured by VAS (0-100) at day 1 (T0), at the day of the last infusion (day 10; T1) and 50 days later (T2). As secondary endpoints, the following clinical assessments were performed: the Western Ontario and MacMaster Universities Osteoarthritis Index (WOMAC) pain questionnaire; the McGill Pain Questionnaire and the 36-Item Short Form Health Survey (SF-36) questionnaire to assess the patient's functional status. All these instruments were administered at T0 and T2. As additional endpoint, changes in WORMS score before the treatment and at T2 have been measured.

Results

Sixty-eight patients were recruited and randomized to treatment with sodium neridronate or placebo in two equal groups (34 patients). At entry, the two groups were well balanced for demographic and clinical characteristics (Table 1).

TABLE I

Demographic, clinical and MRI characteristics of patients with painful knee OA, prior to the beginning of treatment with neridronate or placebo (baseline). Variables are expressed as average value ± corresponding standard deviations

| | Neridronate N = 34 | Placebo N = 34 | P* |
|---|---|---|---|
| Age | 64.7 ± 11.8 | 67.0 ± 7.3 | 0.1 |
| Gender (M/F): | 19/15 | 18/16 | 0.6 |
| BMI (Kg/m$^2$) | 25.7 ± 3.6 | 25.5 ± 3.9 | 0.7 |
| Pain duration (weeks) | 8.1 ± 2.2 | 6.8 ± 2.7 | 0.039 |
| VAS score | 59.0 ± 14.7 | 64.8 ± 16.9 | 0.1 |
| WOMAC | 232 ± 79 | 254 ± 86 | 0.4 |
| SF-36 physical component | 36.6 ± 10.2 | 33.4 ± 6.7 | 0.4 |
| SF-36 mental component | 56.1 ± 12.4 | 59.4 ± 13.2 | 0.1 |
| McGill | 14.3 ± 7.6 | 16.3 ± 12.5 | 0.9 |
| WORMS score | 6.3 ± 3.0 | 7.7 ± 3.9 | 0.1 |

*Mann-Whitney U Test

BMI: Body mass index;

WOMAC: Western Ontario and MacMaster Universities Osteoarthritis index;

SF-36: 36-item Short Form Health Survey;

VAS: visual analog scale;

McGill: McGill pain questionnaire;

WORMS: Whole-Organ MRI score for knee OA.

Only the time elapsed since pain onset resulted slightly but significantly shorter in the placebo group. Fifty-six patients completed the study. One of the patients in the sodium neridronate group withdrew the consent for an adverse event (acute phase reaction) after the first infusion and one patient was excluded because of analgesic resumption before the last clinical evaluation. Eight patients in the placebo group were excluded for the resumption of analgesic or NSAIDs treatment during the study (7 patients) and one patient refused to return to be evaluated 50 days after the treatment. Two patients (one in the sodium neridronate group and one in the placebo group) were excluded because they presented—at the MRI performed at the end of the study—features evocative for an alteration of the joint bone profile evocative for a possible osteonecrosis (flattening/depression of the femoral condyle surface). The distribution of patients is shown in FIG. 1.

Figure 2:
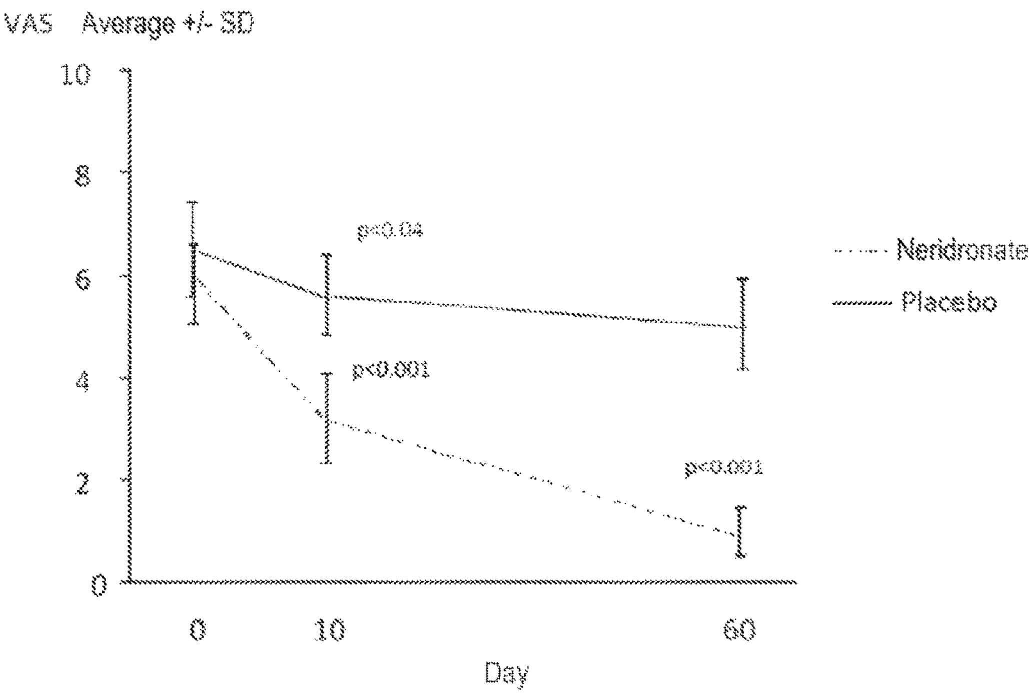
FIG. 2 shows the trend of the VAS parameter during the 60 days following the beginning of treatment of patients according to the study of Example 1.

When VAS score was assessed at the day of the last infusion, both groups showed a significant decrease in comparison with basal values even if a higher significant difference was observed in the sodium neridronate group (FIG. 2). VAS score changed from 59.0±14.7 to 30.4±15.6 in the sodium neridronate group ($p<0.001$), while in the placebo group it decreased from 64.8±16.9 to 55.4±17.4 ($p=0.04$). The comparison between groups at the day of the last infusion showed a significant greater decrease in the group of patients treated with sodium neridronate ($p<0.001$).

After the following 50 days, no further improvement in VAS score was observed in the placebo groups (FIG. 2) and the other clinical measures showed no change in the placebo before and after the treatment (Table 2).

TABLE 2

Clinical characteristics of patients with painful knee OA, treated with neridronate or placebo, 50 days after the end of treatment. Variables are expressed as average value ± corresponding standard deviations

| | Neridronate N = 31 | Placebo N = 25 | P* |
|---|---|---|---|
| VAS score | 9.4 ± 10.8† | 50.1 ± 16.9 | 0.001 |
| WOMAC | 58 ± 58† | 228 ± 162 | 0.001 |
| SF-36 physical component | 51.1 ± 8.7† | 39.3 ± 19.1 | 0.01 |
| SF-36 mental component | 62.5 ± 11.1‡ | 58.3 ± 13.8 | 0.2 |
| McGill | 3.7 ± 4.6† | 15.6 ± 10.8 | 0.001 |
| WORMS score | 3.7 ± 4.2‡ | 7.1 ± 3.6 | 0.002 |

*Mann-Whitney U Test
P vs basal values:
†0.001;
‡0.01 (Wilcoxon signed rank test)
VAS: visual analog scale;
WOMAC: Western Ontario and MacMaster Universities Osteoarthritis index;
SF-36: 36-Item Short Form Health Survey;
McGill: McGill pain questionnaire;
WORMS: Whole-Organ MRI score for knee OA.

At the last clinical evaluation, the sodium neridronate group showed a further significant pain improvement with a VAS score which fell to 9.4±10.8 ($p<0.001$ vs both T0 and T1 values). Also, other pain and functional rating indices showed significant decreases in comparison both with basal values and with placebo treated patients (Table 2).

The WORMS score revaluated at T2 showed a significant decrease in lesion size only in the sodium neridronate group (from 6.3±3.0 to 3.7±4.2; p=0.01), while no significant change was observed in placebo treated group (Table 2). Multivariate regression analyses on clinical variables in patients treated with sodium neridronate demonstrated a correlation close to significance between the VAS decrease observed on the day of the last infusion (T1) and the VAS decrease observed at the end of the study ($\beta=0.452$, p=0.01). When the patients were interviewed by phone two months after the last clinical evaluation, 18 patients out of 25 treated with placebo (i.e. as many as 72%) had resumed analgesic drugs or NSAIDs, while only 4 patients out of 31 treated with sodium neridronate (i.e. only 12.9%) had resumed the symptomatic therapy with analgesic drugs or NSAIDs.

The results of this randomized controlled study therefore provide evidence that sodium neridronate can be effectively used for treating patients with OA.

In particular, the results of this study demonstrated that sodium neridronate can be effectively used for reducing mild, moderate or severe pain symptoms in patients with OA, and specifically moderate or severe symptoms, in patients with OA.

Specifically, sodium neridronate can be effectively used for reducing pain symptoms in patients with OA having basal VAS≥(greater than or equal to) 30 mm.

Specifically, a course of sodium neridronate administered intravenously can be effectively used for treating patients with OA, and in particular for reducing mild, moderate or severe pain symptoms, and specifically moderate or severe symptoms, in patients with OA.

In particular, the study demonstrated that a course of sodium neridronate administered intravenously reduces the pain intensity in patients with symptomatic knee OA.

The study also demonstrated that the size and extent of BMLs decreased significantly in patients treated with sodium neridronate compared to patients treated with a placebo.

That is, sodium neridronate can be effectively used for treating patients with OA undergoing acute painful poussées, reducing the extent of bone marrow lesions.

Finally, the study demonstrated that the treatment of patients with OA with sodium neridronate allowed an effective and long lasting symptomatic treatment, and thereby pain control, at least more than 50 days since the end of treatment.

The advantageous results achieved by the present invention in the treatment of osteoarthritis, especially in the treatment of mild, moderate or severe pain symptoms in patients with OA, are therefore evident from the above description, especially considering that these results were unexpected in view of the prior art related to BPs, especially to aminobisphosphonates, such as risedronate.

The invention claimed is:

1. A method of treating bone marrow lesions consisting of administering to a human patient in need thereof a therapeutically effective amount of a pharmaceutical composition consisting of neridronic acid or a salt thereof and at least one pharmaceutically acceptable vehicle, wherein said treatment of bone marrow lesions reduces joint pain and reduces size and extent of bone marrow lesions, wherein said neridronic acid or the salt thereof is administered intravenously at a dosage of 200 mg, at least 2 times over a period of 5-15 days, with at least 1 day between an administration and a subsequent administration.

2. The method of claim 1, wherein said treatment alleviates joint stiffness and improves mobility and physical functionality.

3. The method of claim 1, wherein said neridronic acid or the salt thereof is sodium neridronate.

4. The method of claim 1, wherein said pharmaceutical composition comprises sodium neridronate, sodium chloride, citric acid and sodium citrate or sodium neridronate, sodium chloride and sodium bicarbonate.

5. The method of claim 1, wherein said therapeutically effective amount of the neridronic acid or the salt thereof is in a vial or bottle for intravenous administration comprising an aqueous solution of the neridronic acid or the salt thereof.

6. The method of claim 5, wherein said neridronic acid or the salt thereof is sodium neridronate.

* * * * *